United States Patent [19]

Kubalak et al.

[11] Patent Number: 5,275,587
[45] Date of Patent: Jan. 4, 1994

[54] APPLICATOR FOR EXTERNAL CATHETER AND METHOD OF USING SAME

[75] Inventors: Thomas Kubalak, Plymouth; Daniel Welch, Zimmerman, both of Minn.

[73] Assignee: Mentor Corporation, Santa Barbara, Calif.

[21] Appl. No.: 873,381

[22] Filed: Apr. 24, 1992

[51] Int. Cl.⁵ .............................................. A61F 5/44
[52] U.S. Cl. .................................... 604/349; 604/355
[58] Field of Search .................... 604/346, 349, 351-

[56] References Cited

U.S. PATENT DOCUMENTS 4,840,187 6/1989 Brazier ................................ 604/349

FOREIGN PATENT DOCUMENTS 2120102 11/1983 United Kingdom ................ 604/349

Primary Examiner—Randy C. Shay
Attorney, Agent, or Firm—Blakely, Sokoloff, Taylor, Zafman

[57] ABSTRACT

An applicator for an external male urinary catheter is described for applying and securing a catheter to a user. The applicator has a solid cylinder preferably with slits surrounded by a flexible skirt on which the catheter is installed, and the cylinder causes the skirt to invert to apply the catheter to the user.

24 Claims, 4 Drawing Sheets

APPLICATOR FOR EXTERNAL CATHETER AND METHOD OF USING SAME

BACKGROUND OF THE INVENTION

1. Field of the Invention

The invention relates to an applicator for the application of an external catheter for male urinary incontinence apparatus, wherein the catheter comprises a soft elastic thin-walled, substantially cylindrical body portion which is open at one end to receive a penis and is narrow at the opposite end for connection to a suitable collection or drainage receptacle. The present invention is also directed to a method of applying a male catheter using the apparatus described herein.

2. Art Background

External male catheters generally take the form of an elastic penile sheath connected at its distal end to a drainage tube that, in use of the device, leads to a suitable collection receptacle. Such a catheter is typically held in place by a pad or coating of pressure sensitive adhesive, or by adhesive applied directly to the interior walls of the catheter. Such sheath has an inner sleeve that sealingly but non-adhesively engages the glans of a patient's penis, the inner sleeve being held in position by a coating or pad of adhesive material in contact with the penile shaft on the glans. U.S. Pat. No. 4,963,137 to Heyden and U.S. Pat. No. 4,640,688 to Hauser disclose such an external catheter.

Since the users of such articles are often elderly persons under nursery or disabled persons, the application of such devices must frequently be performed by the nursing personnel. However, such application is often considered embarrassing to the patients. The act of applying the device may be embarrassing to the care giver as well, since he or she would prefer not to touch the patient's genitals. In order to remedy these disadvantages, applicators for use in the application of an external catheter have been suggested. The applicators are delivered to the user with the catheter disposed thereon so that the user need only uncap the applicator and optionally remove release paper if provided, to expose the adhesive, apply the catheter and disengage the applicator. Relevant catheters and applicators are disclosed in U.S. Pat. Nos. 4,540,409, 4,586,974, 4,589,874, 4,759,753 and 4,894,059 and U.S. Des. Pat. No. 299,865.

Adhesive means, preferably an internal coating of pressure sensitive adhesive, may be used to secure the sheath section to the penile shaft and glans. Ideally, the sheath section includes a non-adhesive portion that is stretched over the glans just behind the urethral meatus to protect the glans against injury that might otherwise be occasioned by prolonged contact with residual amounts of urine that are often retained within an external catheter. The sheath section may optionally include an adhesive to secure the catheter to the penis, although, if no adhesive is provided, the catheter may be retained by the catheter's elastic property or an external or internal adhesive coated tape.

U.S. Pat. No. 4,586,974 shows a catheter with an applicator wherein the applicator is a cylinder on which the catheter is directly installed in an inverted arrangement. The catheter is pushed onto the penis and is forced to slide over the exterior of the applicator smoothly and regularly in order to apply it. This design has several inherent flaws in that the applicator is not very easy to use because it requires the thin and flexible latex sheath of the catheter, which is disposed on the applicator, to be slid over the extensive surface of the applicator. It also requires the penis to be somewhat rigid and equal in length to the sheath in order for the patient or care giver to push the catheter thereon.

U.S. Pat. No. 4,894,059 discloses a catheter applicator having a rolled up catheter which is unrolled as the catheter is applied. A cap is provided over the rolled-up catheter. This device also requires a semi-rigid penis or one with substantial length for easy application of the catheter because the catheter is forced over the end of the penis.

The inherent problems of easy application of the catheter are addressed by the present invention which is described below.

SUMMARY OF THE INVENTION

The present invention comprises an external male catheter and applicator in combination, a method of applying such a catheter to a patient, and a method of making such a catheter.

The applicator of the present invention comprises a generally rigid cylinder having a distal end and a proximal end; an expandable, flexible skirt which is disposed both inside and outside the rigid cylinder such that it is disposed along the inside wall of the cylinder, around the proximal end of the cylinder and then along at least a portion of the outside wall of the cylinder in a slidable arrangement therewith; a means for moving the skirt relative to the cylinder so that at least most of the skirt external to the cylinder is pulled to the inside thereof. More specifically, in the preferred embodiment, the moving means comprises a small handle adapted to be pulled by the fingers of the person applying the catheter, the handle being movable along the axis of the applicator, with the end of the handle adjacent the skirt being connected thereto such that pulling the handle withdraws the skirt from the outside of the cylinder. Alternatively, a handle means is attached to the cylinder, and the skirt is held in a fixed position relative to the handle so that the cylinder is pushed away from the handle causing the fixed skirt to be pulled inside the cylinder, in a similar movement as described above. The cylinder is optionally split with slits disposed along the walls thereof to accommodate larger users. The edge of the cylinder is preferably an enlarged bulbous portion relative to the remainder of the cylinder.

The skirt is a flexible thin material which of relatively low friction which can be slid along the surfaces of the cylinder with minimum resistance. The skirt is made of plastic, leather, or paper. The skirt is made of a material, and made in a conformation which can be inverted as explained in more detail below. In accordance with this purpose, the skirt is preferably, but not necessarily, formed of strips of material connected at one end to a circular band, where the circular band portion connects to the pulling means.

The catheter has an open proximal end intended to go over the shaft of the penis, and a narrow distal end for connection to a urine collection system. The interior portion of the catheter can be coated with a contact adhesive, or used in combination with double-sided adhesive strips as is known in the art, preferably so that it adheres to the glans and/or shaft of the penis in use to provide a secure fit near the end of the penis and to prevent detachment of the catheter while in use. Alternatively, no adhesive is used and the catheter is held in place by tension from the elastic properties of the catheter.

The catheter is installed on the skirt in an inverted arrangement, whereby the interior of a portion of the catheter near its proximal end is facing outward on the applicator. The remainder of the catheter is preferably disposed within the applicator. The catheter is held onto the applicator by the resilience of the rubber or elastic sheath material which is stretched to fit on the applicator. The skirt is at all times between the catheter and the cylinder, both along the inside surface and the outside surface of the cylinder and permits the catheter to be installed on a patient as described below. The narrow distal end of the catheter is disposed within the applicator. To facilitate adherence to the penis, adhesive is sometimes provided and is coated around a portion of the interior and exterior surfaces of the opening to the catheter at its proximal end. Additionally, a release paper and a cap is provided which surrounds the inverted portion of the catheter to prevent any unwanted materials or things from sticking to adhesive or non-adhesive coated areas on the catheter.

To apply the catheter using the applicator of the present invention, the cap is removed exposing the catheter, which is pushed onto the end of the penis until resistance is felt. Then the trigger of the applicator is depressed which either pulls the skirt into the cylinder, or pushes the cylinder over the skirt, in either case rolling the catheter onto the penis in a smooth fashion. Once the catheter is inverted so that the inside is facing inward, it no longer is on the applicator and the applicator can simply be withdrawn.

In making the catheter and applicator, the catheter is formed of latex, silicone or other similar material known in the art, and installed on the applicator with the opening end of the catheter partially inverted and stretched over the cylindrical portion of the applicator so that the end of the skirt is minimally showing past the end of the catheter. The remainder of the catheter is fed through the center of the applicator so that it is disposed within the applicator. During assembly, the cylinder base and leg portion of the applicator are not connected to the cylindrical portion, and therefore the end of the catheter is available and accessible out the distal end of the cylinder. Since the catheter is made sealed at this end, the end may be snipped before the applicator assembly is complete. The remainder of the applicator assembly is attached to the cylinder and the device is capped. The present invention provides a medical care provider with the ability to single-handedly attach a male external catheter to a penis if the penis is not retracted; if retracted, one hand can be used to compress the abdomen to expose the retracted penis while the other hand can be used to actuate the applicator and apply the catheter to the penis.

It is an object of the present invention to provide an easy to use male urinary catheter applicator and assembly which applies a male catheter to a patient with virtually no manual contact or manipulation other than with the applicator itself.

It is another object of the present invention to provide an applicator for a male urinary catheter which permits application of the catheter in a single fast movement.

It is yet another object of the present invention to provide an applicator for a male urinary catheter which smoothly inverts the catheter onto a penis without having to push the catheter onto the penis, but instead allowing it to roll off the surface by virtue of a mechanical movement by the applicator.

It is yet another object of the present invention to provide an improved method of applying an external urinary catheter to a penis.

It is yet another object of the present invention to provide a new method of making the catheter and applicator combination of the present invention.

This and other objects of the present invention may be understood by reference to the drawings and specification set forth below. It will be understood, however, that the present invention is not limited to the specific embodiments shown in the appended drawings or described in the specification, but to the devices and methods as set forth in the claims, and any equivalents thereto.

BRIEF DESCRIPTION OF THE DRAWINGS

FIG. 5A shows the subject applicator combination prior to applying the catheter to a penis.

FIG. 5B shows the subject applicator being used to apply the catheter to the end of the penis.

FIG. 5C shows the subject applicator being actuated to apply the remainder of the catheter to the penis.

FIG. 5D shows the subject applicator being withdrawn after the catheter has been applied.

FIG. 10A shows the subject applicator prior to applying the catheter to a penis.

FIG. 10B shows the subject applicator being used to apply the catheter to the end of the penis.

FIG. 10C shows the subject applicator being actuated to apply the remainder of the catheter to the penis.

FIG. 10D shows the subject applicator being withdrawn after the catheter has been applied.

DETAILED DESCRIPTION OF THE INVENTION

Figure 1:
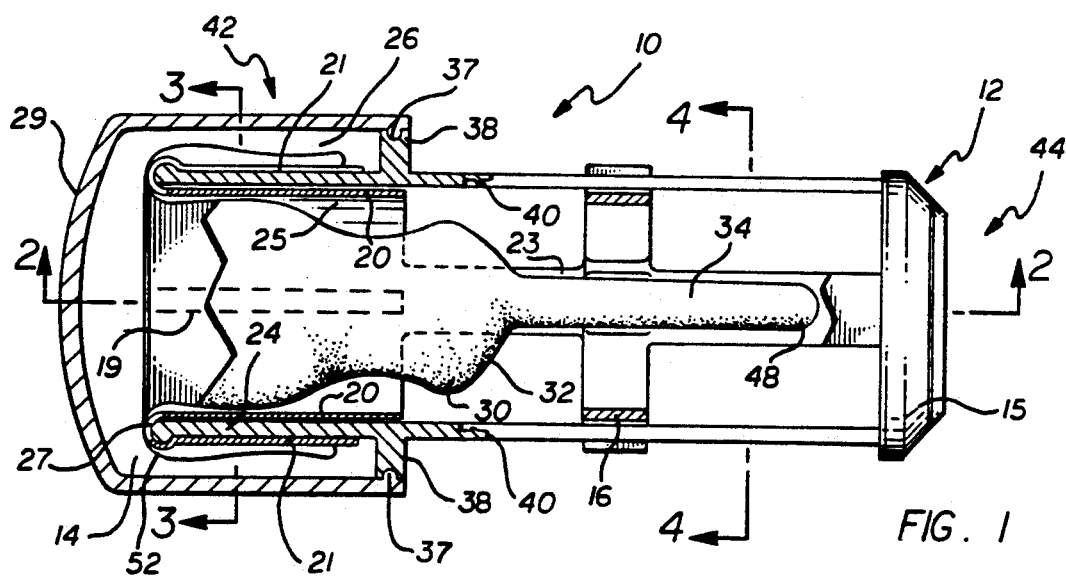
FIG. 1 is a longitudinal partial sectional view of the preferred embodiment of the combination of the subject applicator and catheter.
Figure 2:
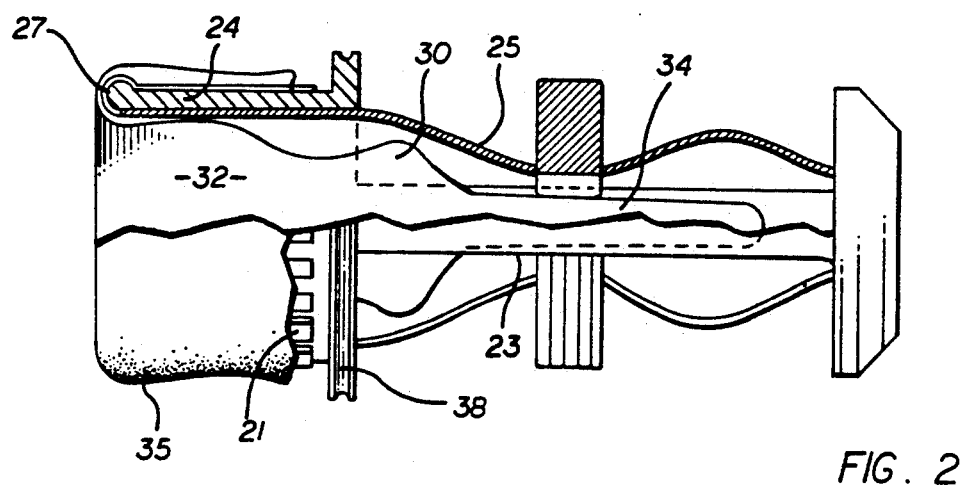
FIG. 2 is a partial sectional, cross-sectional view of the subject applicator and catheter of FIG. 1 taken through lines 2—2 of FIG. 1.

As shown in FIG. 1, the preferred embodiment of the present invention comprises generally a housing 10 having a distal end 12 and a proximal end 14. A handle means 15 is provided on the distal end and a pulling means or trigger 16 is provided near the middle of the housing 10. The pulling means 16 is slidably connected to the housing 10 so that it moves axially therewithin. The pulling means 16 is connected to a skirt 20. The skirt 20 surrounds an applicator cylinder 24 which forms a portion of the housing 10. The skirt 20 is made of a flexible, non-sticking material such as a plastic on at least one surface. It is preferably formed primarily of a plurality of strips 21 which permit radial expansion and contraction, as well as for inversion as described below. While it will be understood by persons of skill in the art that any arrangement of the connection between the pulling means 16 and the skirt 20 can be utilized in accordance with the scope of the present invention, in the preferred embodiment, the skirt 20 comprises the strips 21, as shown in FIG. 2. The applicator cylinder 24 has, in its preferred embodiment, a pair of slits 19 which permit jaws-like expansion of the cylinder to accommodate larger users during the application of the catheter, although, one or more slits may work to provide the necessary expansion.

The strips 21 are disposed adjacent the applicator cylinder 24, with one surface or side of the skirt contacting the cylinder 24. Specifically, the strips 21 are adjacent the exterior of the cylinder 24, and go around the proximal end 27 of the cylinder 24 and then are disposed along the interior surface of the cylinder 24 where they connect to the skirt 20 and pulling means 16 through connecting means 25 and optionally to the handle 15. The proximal end 27 of the cylinder 24 is preferably an enlarged bulbous or rounded portion relative to the remainder of the cylinder 24 as shown in FIG. 1. Pulling means 16 slides along axial guide 23 shown partially in ghost lines in FIGS. 1 and 2. As pulling means 16 moves toward the distal end of the housing 10, it pulls the skirt 20 distally through the interior of the connecting means 25 of the cylinder 24, around the end 27 causing the exteriorly disposed skirt 20 to move proximally. Connecting means 25 is preferably a flexible, resilient material which can bend to conform to any shape when retracted when the pulling means 16 is actuated.

A male external catheter 30 is disposed, as shown in FIGS. 1 and 2, primarily in the interior of the housing 10. It wraps around end 27 and the end of catheter 30 is disposed over the skirt 20 and strips 21 which in turn is disposed over the cylinder 24. The catheter 30 is stretched over the strips 21 and cylinder 24 snugly and is retained thereon by tension from the material. The catheter 30 is made of thin flexible natural or synthetic water-tight material such as latex, silicone rubber or other elastomeric material. It has a main body portion 32 of sufficient width to tightly fit over the typical male penis, and a narrow portion 34 which connects to a collection bag or similar device in use. The interior surface 35, which is facing exteriorly when installed on the applicator, is preferably coated with a contact adhesive as is known in the art. The use of contact adhesive is optional, however.

Figure 3:
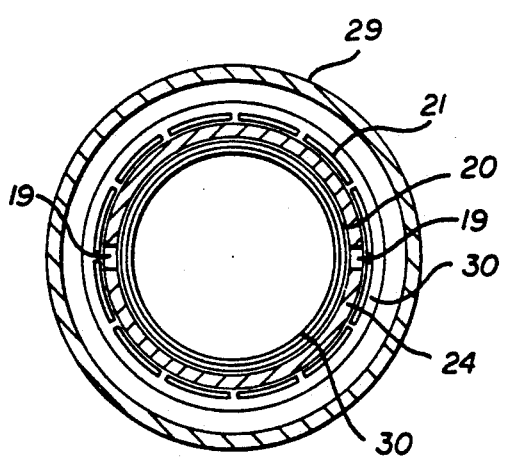
FIG. 3 is a cross-sectional view of the subject applicator and catheter of FIG. 1 taken through lines 3—3 of FIG. 1.
Figure 4:
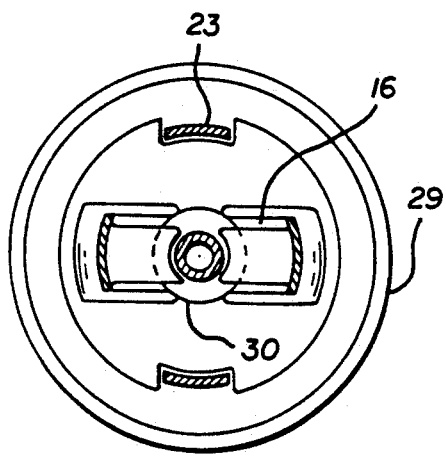
FIG. 4 is a cross-sectional view of the subject applicator and catheter of FIG. 1 taken through lines 4—4 of FIG. 1.

As shown in FIG. 3, the catheter 30 is the innermost layer, and is adjacent the skirt 20, which is adjacent the cylinder 24, which is adjacent the strips 21 on the outer portion of the cylinder, which is adjacent the catheter 30 on the outside of the cylinder. A cap 29 is provided to prevent the adhesive treated portion 35 of the catheter 30 from contacting anything unintentionally until the catheter 30 is applied to a patient. The cap 29 is preferably a snap-fit although any connecting means known or used in the art can be adapted for the intended purpose herein. As shown in FIGS. 1 and 4 the cap 29 has a flange 37 which fits within a recess 38 in the housing 10.

In manufacturing the preferred embodiment of the present invention, the housing is made in two parts, the proximal unit 42 and the distal unit, 44 which are joined together at the connecting point 40. This arrangement permits easy manufacture as described below. Additionally, the catheters in general are made with the narrow end 34 sealed, and the sealed end 48 is clipped open before shipment. Accordingly, by applying the catheter to the proximal unit 42 before the distal unit 44 is connected therewith, the end 48 is accessible and easily clipped. The distal unit 44 is then attached. The adhesive coating can then optionally be applied to the catheter 30. The cap 29 can then be attached to the recess 38 to enclose the catheter 30.

Figure 5A:
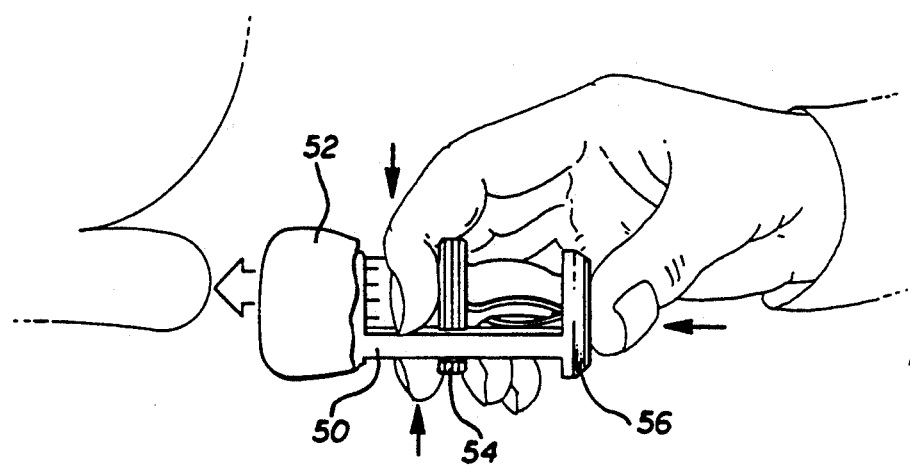
FIGS. 5A-5D illustrate the method of using the applicator of the preferred embodiment shown in FIGS. 1-4 to apply a male catheter to a penis of a patient.

Use of the preferred embodiment of the present invention is shown in FIGS. 5A-5D. In FIG. 5A, the applicator 50 with the catheter 52 attached is advanced to a penis in the direction shown by the arrow. The applier's fingers grip the pulling means 54 and the handle 56 preparing for a squeezing motion which will move the pulling means 54 and handle 56 closer together.

Figure 5B:
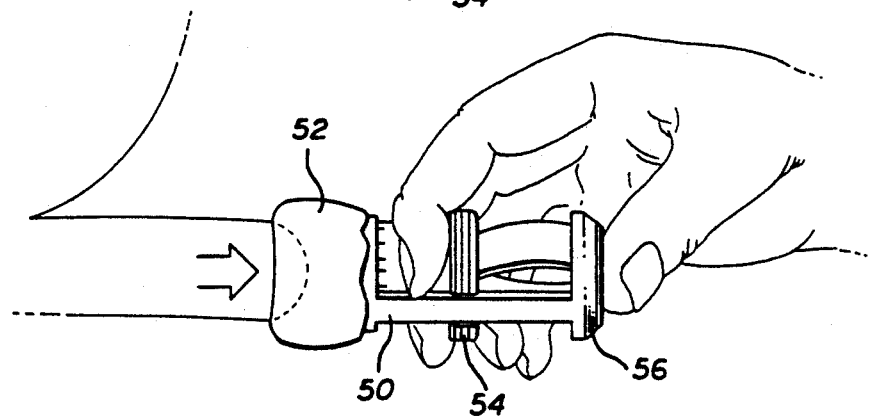
Figure 5C:
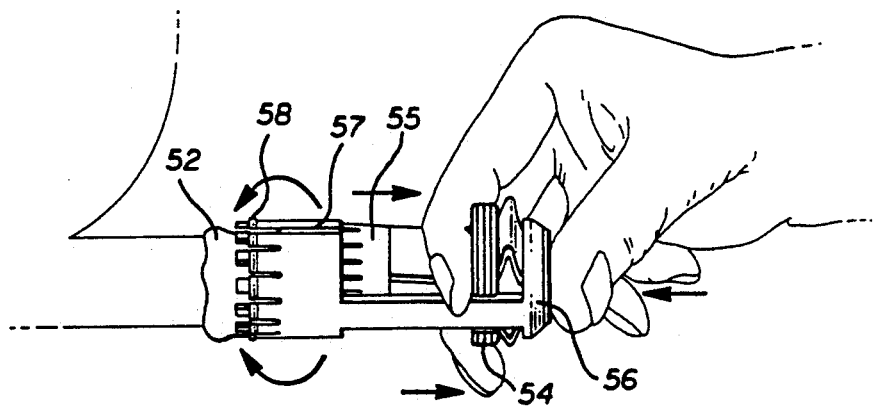
Figure 5D:
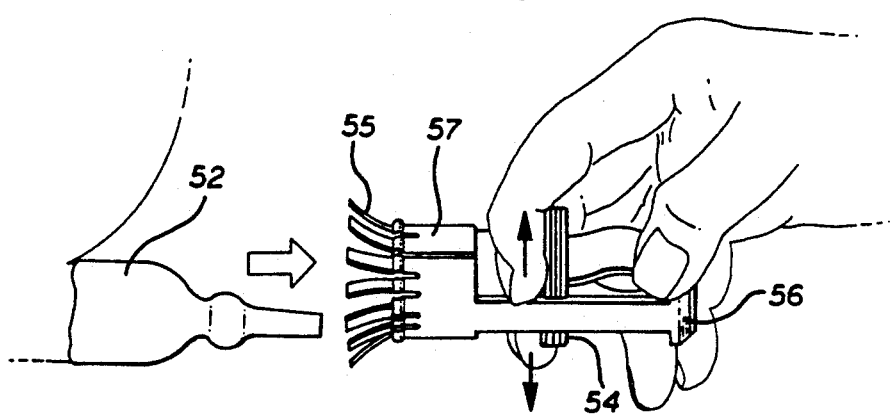
Figure 6:
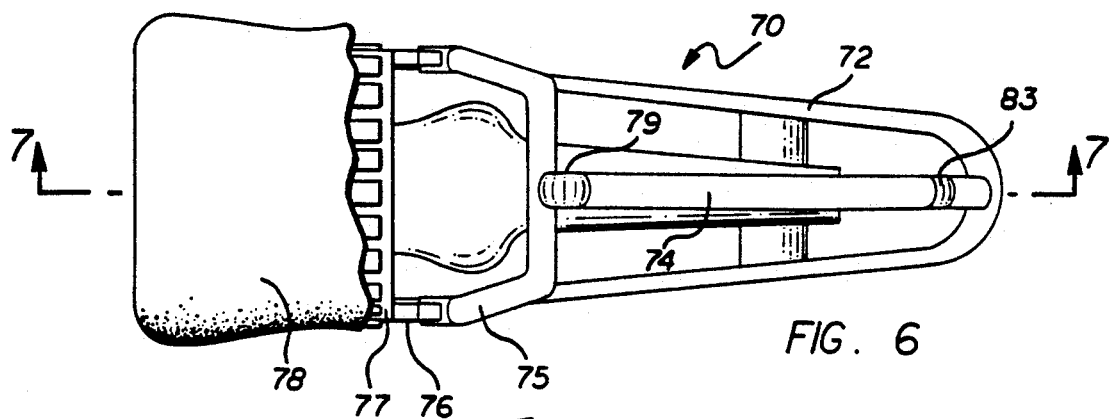
FIG. 6 is a longitudinal view of the an alternative embodiment of the combination of the invented applicator and catheter.

As shown in FIG. 5B, the applicator 50 is positioned so that the catheter 52 contacts the penis. The catheter 52 is pushed onto the penis so that the adhesive portion (not shown) of the catheter adheres to the glans of said penis, and then is withdrawn in the direction of the arrow pulling the penis outward from the body. As shown in FIG. 5C, the applicator is advanced along the penis as the pulling means 56 is retracted, withdrawing the skirt 55 into and through the cylinder 57. This causes the catheter 52 to invert as shown by the curved arrows, because the skirt is pulled through the cylinder so that as it comes around end 58 of the cylinder it inverts bringing the catheter 52 with it. The end 58 of the cylinder 57 is preferably an enlarged bulbous or rounded portion relative to the remainder of the cylinder 57 as shown in FIG. 5C. With the catheter 52 inverted, the adhesive portion inside of the catheter 52 faces inward onto the skin and forms a secure fit and seal. The applicator is then free to be withdrawn as shown in FIG. 5D.

In a second embodiment of the present invention shown in FIGS. 6-10 (including FIGS. 10A-10D), the applicator holds the skirt in a fixed position relative to the housing of the applicator, and the cylinder moves forward relative to the housing of the applicator to effect the inversion of the catheter disposed on the skirt. This second embodiment differs from the preferred embodiment described above in that in the preferred embodiment the skirt moves relative to the housing and cylinder which remain in fixed position relative to each other. Although not shown, this embodiment may also have a slit in the applicator cylinder to accommodate larger user as described above.

Figure 7:
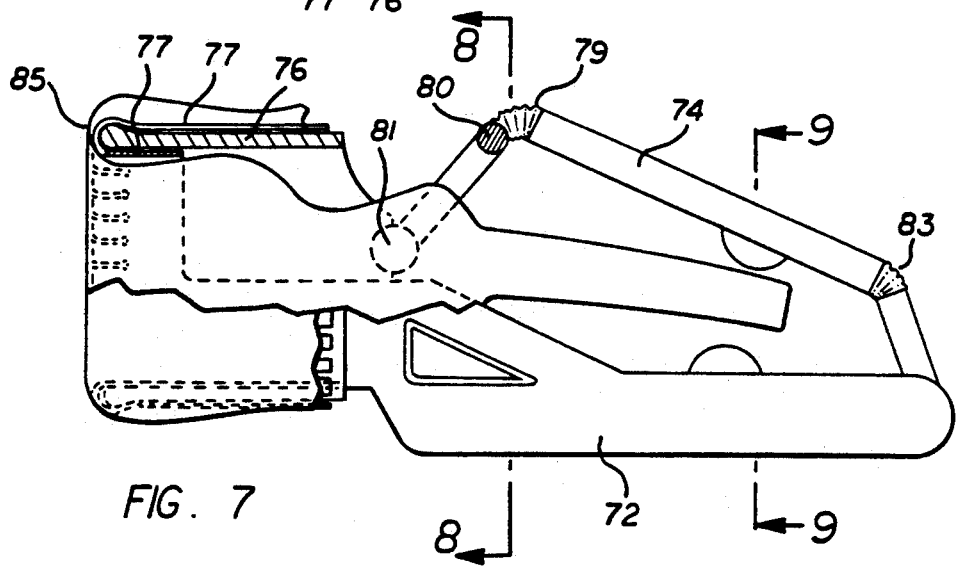
FIG. 7 is a partial sectional, cross-sectional view of the subject applicator and catheter of FIG. 6 taken through lines 7—7 of FIG. 6.
Figure 8:
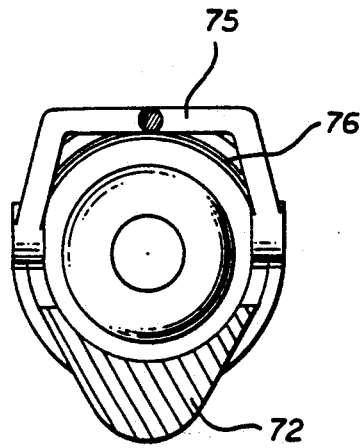
FIG. 8 is a cross-sectional view of the subject applicator and catheter of FIG. 6 taken through lines 8—8 of FIG. 7.
Figure 9:
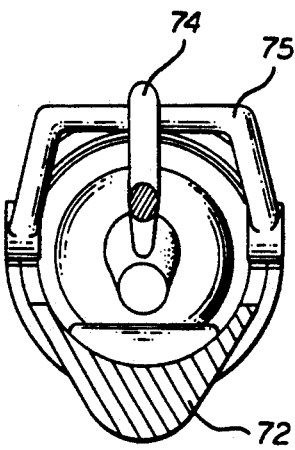
FIG. 9 is a cross-sectional view of the subject applicator and catheter of FIG. 6 taken through lines 9—9 of FIG. 7.

More specifically as shown in the figures, the applicator 50 comprises generally a housing 72, an actuator 74, a cylinder pushing means 75, a cylinder 76, a skirt 77 and the catheter 78 which is the same as the catheter described above. The actuator 74 has three flex points 79, 81 and 83 which permit it to move relative to the pushing means and housing respectively, in the manner demonstrated in FIGS. 10A-10D. The basic configuration of the skirt 77, cylinder 76 and catheter 78 relative to each other is the same as described above with reference to the first embodiment, with the skirt 77 being disposed adjacent the cylinder 76, and wrapped around the end 85 of the cylinder 76. The catheter 78 is disposed adjacent the skirt 77 and is also wrapped around the end 85 of the cylinder (over the skirt 77). The end 85 of the cylinder 76 is preferably an enlarged bulbous or rounded portion relative to the remainder of the cylinder 76 as shown in FIG. 7. As mentioned above, in this embodiment, the cylinder 76 may have slits (not shown) like the previously described embodiment.

Figure 10A:
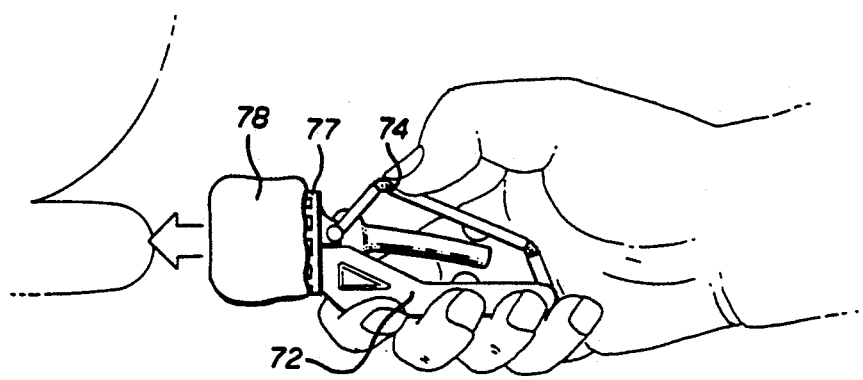
FIGS. 10A-10D illustrate the method of using the applicator of the preferred embodiment shown in FIGS. 6-9 to apply a male catheter to a penis of a patient.
Figure 10B:
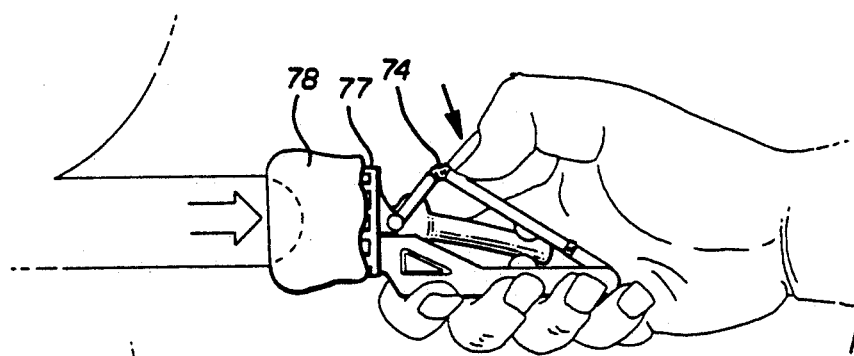
Figure 10C:
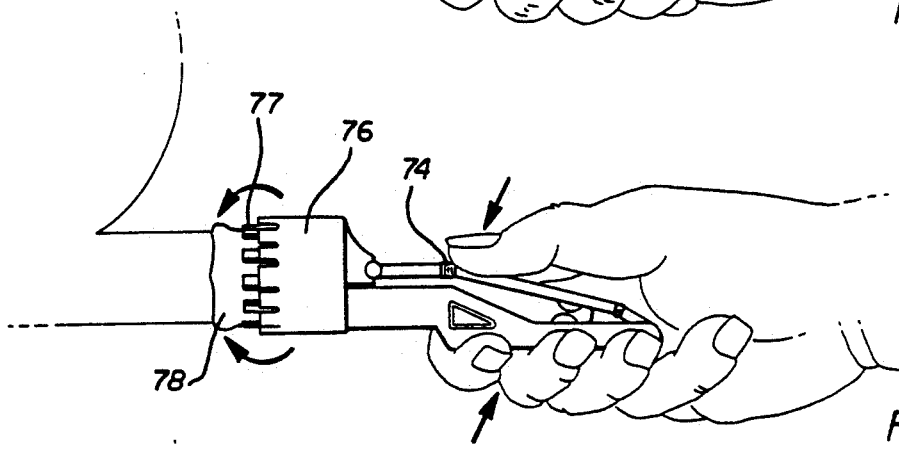
Figure 10D:
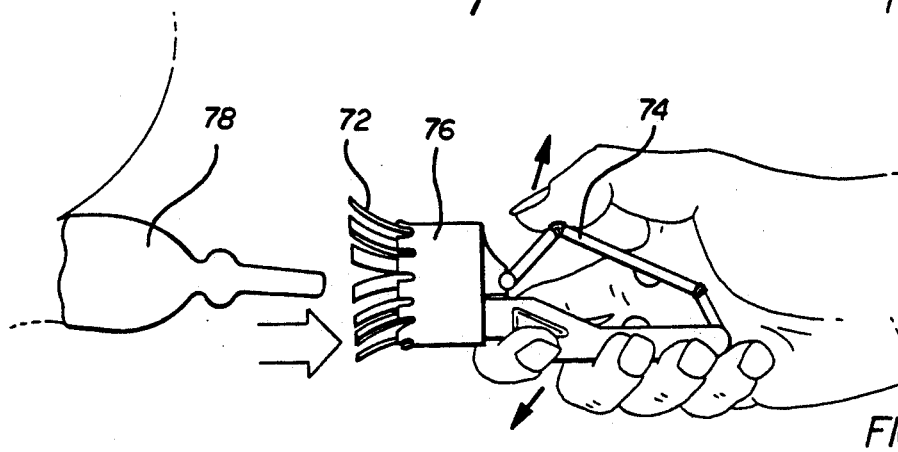

The actuator 74 is attached to the cylinder 76 such that when the actuator is depressed as shown in FIG. 10C, the cylinder 76 is pushed in a proximal direction via the pushing means 75 while the skirt 77 and the catheter 78 remain fixed in position relative to the housing 72. This causes the cylinder 76 to push the catheter 78 and skirt 77 inside it, which causes inversion of the catheter 78 and skirt 77.

In order to apply a catheter, as shown in FIGS. 10A through 10D, the applicator 70 with the catheter 78 installed thereon, is advanced to a penis as shown in FIGS. 10A and 10B. When the penis is contacted and the catheter is advanced onto the penis (FIG. 10B), the actuator 74 is depressed. This causes the cylinder 76 to be advanced proximally, inverting the skirt 77 and catheter 78 as shown by the arrows (FIG. 10C). The subsequent release of the actuator causes the cylinder 76 to retract distally.

Other designs, particularly for different catheters, and actuation designs can be used by those skilled in the art to implement the present invention without departing from the spirit and scope of the present invention. Other types of adhesive, including adhesive strips with release paper on the outer side thereof as well as contact adhesive may be optionally applied as well to retain the catheter on the penis.

What is claimed is:

1. An applicator for an external male catheter, wherein said catheter comprises a sheath of thin, stretchable, elastic material having a general cylindrical shape and including a portion with a larger diameter, a tapered neck section and a narrow diameter portion for connection to an outlet, wherein said applicator comprises:
   a housing for containing therewithin most of said catheter, said housing having a distal end and a proximal end;
   a cylinder disposed on said proximal end of said housing, said cylinder having an inside and outside surface and a distal and proximal end, wherein the proximal end of the cylinder is rounded and is thicker than the remainder of said cylinder.
   a skirt means having an inside and an outside surface, said skirt means being disposed inside and outside said cylinder and around said proximal end of said cylinder, such that said skirt means is folded back on said cylinder in an inverted position thereon with a portion of the inside surface of said skirt means facing outward, and said skirt means comprising a plurality of separate adjacent strips of material attached at one end;
   an actuating means for moving said skirt means relative to said cylinder such that upon actuation thereof, said means is moved to a position primarily within said cylinder,
   and wherein, in use, said catheter is partially disposed within said skirt means at the portion of said skirt means within said cylinder, and around said skirt means on the portion of said skirt means outside of said cylinder,
   whereby when said skirt means is retracted into said cylinder or said cylinder is moved over said skirt means, said skirt means and said catheter are inverted so that inside surfaces thereof face inward.

2. The applicator of claim 1 wherein said actuating means is connected to said skirt means, and said cylinder is connected to said housing.

3. The applicator of claim 2 wherein said actuating means is axially movable through said housing, whereby said skirt means is retracted into said cylinder upon actuation.

4. The applicator of claim 1 wherein said skirt means comprises material which slides freely on said cylinder.

5. The applicator of claim 1 wherein said actuator means is detachably attached to said cylinder and said housing is connected to said skirt means.

6. The applicator of claim 1 wherein said actuator means comprises a raised flange which when moved toward said housing moves said cylinder proximally thereby drawing said skirt means therewithin.

7. The applicator of claim 1 further comprising a cap means disposed over said housing distal end so that in use it surrounds said catheter.

8. The applicator of claim 1 further comprising at least one slit disposed in said cylinder to permit radial expansion of said cylinder.

9. An applicator for an external male catheter, wherein said catheter comprises a sheath of thin, stretchable, elastic material having a general cylindrical shape and including a portion with a larger diameter at a proximal end thereof, a tapered neck section and a narrow diameter portion for connection to an outlet at a distal end thereof, and wherein said applicator comprises:
   a housing for containing therewithin most of said catheter, said housing having a distal end and a proximal end;
   a cylinder disposed on said proximal end of said housing, said cylinder having an inside and outside surface and a distal and proximal end, said cylinder having a pair of slits opposite each other, and the proximal end of said cylinder comprising an enlarged bulbous portion relative to the remainder of the cylinder;
   a skirt means having an inside surface and an outside surface, said skirt means being disposed inside and outside said cylinder and around said proximal end of said cylinder, such that said skirt means is folded back on said cylinder in an inverted position thereon with a portion of the inside surface of said skirt means facing outward, said skirt means comprising a plurality of strips of material;
   an actuating means for moving said skirt means relative to said cylinder such that upon actuation thereof, said skirt means is moved to a position primarily within said cylinder;

and wherein, in use, said catheter is partially disposed within said skirt means at the portion of said skirt means within said cylinder, and around said skirt means on the portion of said skirt means outside of said cylinder;

whereby when said skirt means is retracted into said cylinder or said cylinder is moved over said skirt means, said skirt means and said catheter are inverted so that the inside surfaces thereof face inward.

10. A method of applying an external catheter to a patient using only one hand comprising:
providing an applicator of claim 1 with a catheter disposed thereon, said catheter comprising a sheath of thin, stretchable, elastic material having a general cylindrical shape and including a portion with a larger diameter at a proximal end thereof, a tapered neck section and a narrow diameter portion for connection to an outlet at a distal end thereof, and wherein a portion of catheter near the proximal end is coated with adhesive;
advancing said catheter such that the tapered section of the catheter abuts the end of the penis of the patient so that the adhesive portion adheres to the glans of the penis;
pulling said applicator so as to extend said penis;
actuating said actuating means to cause the skirt means to be withdrawn into the cylinder, thereby inverting said catheter and applying it to the penis; and
withdrawing the applicator from the penis.

11. The method of claim 10 wherein is said actuating means pushes said cylinder proximally thereby withdrawing said skirt means through said cylinder.

12. The method of claim 10 wherein said actuating means pulls said skirt means through said cylinder.

13. A combination assembly of a male external catheter and applicator therefor, the combination comprising:
said catheter comprising a sheath of thin, stretchable, elastic material having a general cylindrical shape and including a portion with a larger diameter, a tapered neck section and a narrow diameter portion for connection to an outlet, wherein said applicator comprises:
a housing for containing therewithin most of said catheter, said housing having a distal end and a proximal end;
a cylinder disposed on said proximal end of said housing, said cylinder having an inside and outside surface and a distal and proximal end, wherein the proximal end of the cylinder is rounded and is thicker than the remainder of said cylinder;
a skirt means having an inside and an outside surface, said skirt means being disposed inside and outside said cylinder and around said proximal end of said cylinder, such that said skirt means is folded back on said cylinder in an inverted position thereon with a portion of the inside surface of said skirt means facing outward, and said skirt means comprising a plurality of separate, adjacent strips of material attached together at one end;
an actuating means for moving said skirt means relative to said cylinder such that upon actuation thereof, said means is moved to a position primarily within said cylinder, said actuating means connected to said attached together end of said skirt means, and wherein, in use, said catheter is partially disposed within said skirt means at the portion of said skirt means within said cylinder, and around said skirt means on the portion of said skirt means outside of said cylinder, whereby when said skirt means is retracted into said cylinder or said cylinder is moved over said skirt means, said skirt means and said catheter are inverted so that inside surfaces thereof face inward.

14. The combination assembly of claim 13 wherein said actuating means is connected to said skirt means, and said cylinder is connected to said housing.

15. The combination assembly of claim 14 wherein said actuating means is axially movable through said housing, whereby said skirt means is retracted into said cylinder upon actuation.

16. The applicator of claim 13 wherein the portion of said catheter which is near the distal end and is inverted on the skirt is coated with a contact adhesive.

17. The combination assembly of claim 13 wherein said distal end of said catheter is entirely disposed within said housing.

18. An applicator for an external male catheter, wherein said catheter comprises a sheath of thin, stretchable, elastic material having a general cylindrical shape and including a portion with a larger diameter, a tapered neck section and a narrow diameter portion for connection to an outlet, and wherein said applicator comprises:
a housing for containing therewithin most of said catheter, said housing having a distal end and a proximal end;
a cylinder disposed on said proximal end of said housing, said cylinder having an inside and outside surface and a distal and proximal end, and at least one slit disposed in said cylinder to permit radial expansion of said cylinder;
a skirt means having an inside surface and an outside surface, said skirt means being disposed inside and outside said cylinder and around said proximal end of said cylinder, such that said skirt means is folded back on said cylinder in an inverted position thereon with a portion of the inside surface of said skirt means facing outward;
an actuating means for moving said skirt means relative to said cylinder such that upon actuation thereof, said skirt means is moved to a position primarily within said cylinder;
and wherein, in use, said catheter is partially disposed within said skirt means at the portion of said skirt means within said cylinder, and around said skirt means on the portion of said skirt means outside of said cylinder;
whereby when said skirt means is retracted into said cylinder or said cylinder is moved over said skirt means, said skirt means and said catheter are inverted so that the inside surfaces thereof face inward.

19. The applicator of claim 18 wherein said actuating means is connected to said skirt means, and said cylinder is connected to said housing.

20. The applicator of claim 19 wherein said actuating means is axially movable through said housing, whereby said skirt means is retracted into said cylinder upon actuation.

21. The applicator of claim 18 wherein said skirt means comprises a plurality of adjacent strips of material.

22. The applicator of claim 18 wherein said skirt means comprises material which slides freely on said cylinder.

23. The applicator of claim 18 further comprising a cap means disposed over said housing distal end so that in use it surrounds said catheter.

24. The applicator of claim 18 wherein the proximal end of the cylinder is rounded and is thicker than the remainder of said cylinder.

* * * * *